United States Patent [19]

Kuphal

[11] 4,221,371

[45] Sep. 9, 1980

[54] UROLOGICAL EXAMINATION TABLE

[75] Inventor: Wilko Kuphal, Rueckersdorf, Fed. Rep. of Germany

[73] Assignee: Siemens Aktiengesellschaft, Berlin & Munich, Fed. Rep. of Germany

[21] Appl. No.: 967,362

[22] Filed: Dec. 7, 1978

[30] Foreign Application Priority Data

Dec. 30, 1977 [DE] Fed. Rep. of Germany ....... 2758845

[51] Int. Cl.$^3$ .............................................. A61G 13/00
[52] U.S. Cl. ..................................... 269/327; 128/292
[58] Field of Search ....................... 269/327; 128/292; 4/113.1, 114.1, 144.1–144.4; 248/95

[56] References Cited

U.S. PATENT DOCUMENTS

| | | | |
|---|---|---|---|
| 2,959,386 | 11/1960 | Garth | 298/95 |
| 3,386,444 | 6/1968 | Brenner et al. | 269/327 |
| 3,494,356 | 2/1970 | Melges | 128/292 |
| 4,007,741 | 2/1977 | Waldrap et al. | 128/292 |

FOREIGN PATENT DOCUMENTS 1136986 12/1968 United Kingdom ..................... 128/292

*Primary Examiner*—Robert C. Watson

*Attorney, Agent, or Firm*—Hill, Van Santen, Steadman, Chiara & Simpson

[57] ABSTRACT

Hitherto, tub-like collector receptacles capable of being pulled forward in two guide rails in a drawer-like fashion have been utilized. These collector receptacles are bulky, cause interference during the examination process, and, even in the case of a restricted collector-volume, obstruct the knee-freedom of the physician conducting the examination. The disclosure here instead of the rigid collector receptacle, provides a collector receptacle which consists essentially of a plastic sack and a highly flexible band, guided on-edge, through a tubularly flanged border of the plastic sack for supporting the plastic sack. This band can be mounted in countersupports pivotal on the supports of the examination table. The upper edge of the plastic sack can be only partly tubularly flanged with another portion forming an approximately 70-cm-long and approximately 60-cm-wide sheet which can be placed on the patient support platform. This sheet, at its uppermost terminal edge, can be capable of being secured tightly to the body of the patient by means of a belt. At its deepest location, the plastic sack can have a tubular outlet fitting which can be coupled to a corresponding hose connection piece.

14 Claims, 1 Drawing Figure

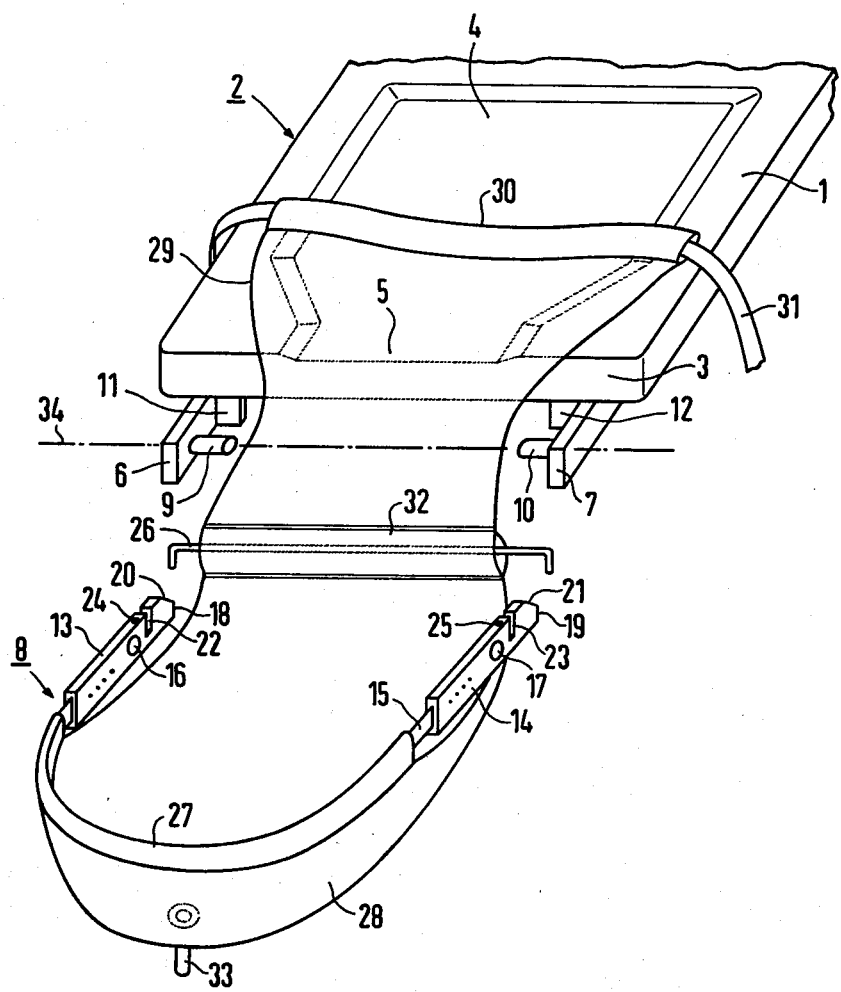

UROLOGICAL EXAMINATION TABLE

BACKGROUND OF THE INVENTION

The invention relates to a urological examination table comprising a patient support platform and comprising a collector receptacle insertable in two supports at the caudal frontal side of the patient support platform directly beneath the same.

In the case of urological examination tables, it is known to position the patient on the patient support platform in the lithotomy position with the posterior near the caudal frontal side of the patient support platform. In order to collect outflowing contrast medium, rinsing (or flushing) fluid, as well as cotton swabs, and the like, such urological examination tables are provided at this frontal side with a collector receptacle which can be pulled forward in a drawer-like fashion. This collector receptacle, in most instances an enameled metal tub, frequently obstructs the examination on account of its bulkiness. On the other hand, however, it cannot be substantially reduced in size, because its collector-volume would otherwise be too greatly restricted. Also, a reduction in its cross-section pursuant to a simultaneous enlargement of its depth would be disadvantageous, because the freedom of movement of the examining individual would be thereby impaired.

SUMMARY OF THE INVENTION

Accordingly, the object underlying the invention consists in producing a collector receptacle which, with a comparable collector-volume, is less obstructive. This collector receptacle should simultaneously be as simple and economical as possible.

Accordingly, in the case of a urological examination table of the type initially cited, in accordance with the invention, the collector receptacle comprises a plastic sack which is flanged and bonded in a tubular fashion at the border and a highly flexible band capable of being coupled at both its ends, by means of countersupports, to the supports of the patient support plate, is guided on edge in a horizontal, essentially semicircular arch as the bearing element through the flanged border of the plastic sack. This has the advantage that the collector receptacle is flexible in its contour facing the examining physician and that it does not obstruct the physician during his work. In addition, such a flexible plastic sack does not obstruct the leg freedom of the individual conducting the examination. Also, upon raising the examination table into an upright position, no danger exists if the plastic sack strikes against the floor or against equipment located on the floor. Finally, such a plastic sack, which can be formed as a disposable article, dispenses with the disinfecting of the collector receptacle otherwise necessary after each examination.

The handling of the collector receptacle can be even better adapted to the examination requirements if the counter-supports, in a particularly advanced further development of the invention, are pivotally mounted on the supports for movement about a horizontal axis aligned parallel to the caudal front face of the examination table. This has the advantage that the collector receptacle, in the case of specific types of work—if e.g. rinsing (or flushing) is carried out and the spraying (or splashing) out of rinsing fluid is expected—can be swung up. It thus better protects the examining individual seated at the caudal front side of the patient support platform from rinsing (or flushing) fluid under these circumstances.

In an advantageous embodiment of the invention, the two supports, at corresponding allochiral sides, can each bear a horizontal pin which is capable of being inserted into a corresponding bore of one of the countersupports, and the countersupports, via a rod fixing their mutual spatial interval, can be connected with one another in a manner preventing twisting. This construction is as simple as it is practical. The two countersupports need only be provided with a bore in order to be guided into the pins of the supports of the examination table. The rod here prevents disengagement from the pins of the supports, and simultaneously couples the two countersupports with one another for joint pivoting movement about the pins. Any torsional forces are thus isolated from the highly flexible band. The band need only take up the load of the plastic sack.

A particularly simple support-mounting of the collector receptacle in its operating position is achieved if there are assigned to the two supports, in an embodiment of the invention, one stopping face each which are capable of being brought into engagement with a corresponding face of the respective countersupport for the purpose of arresting the band in the horizontal plane. This simple construction becomes possible because, due to the simple manner of removing the collector receptacle from its supports, a downward swinging movement is not necessary.

The handling of the collector receptacle becomes more comfortable if, in a particularly advantageous further development of the invention, the stopping faces are aligned parallel to the caudal front face of the examination table, and if the countersupports, in addition to the faces assigned with the horizontal position of the band, manifest an additional auxiliary face each coming into engagement with one of the stopping faces pursuant to swinging up the band 30°. These auxiliary faces produce a clearly noticeable lock-in position for the collector receptacle. The collector receptacle can remain in this swung-up lock-in position during the rinsing operation.

A contamination of the examination table is effectively prevented if, in a particularly expedient further development of the invention, only a portion of the upper border of the plastic sack is provided with a tubular flange, and another portion forms an approximately 70-cm-long and approximately 60-cm-wide sheet. This has the advantage that the sheet can be placed on the examination table and beneath the patient. Outflowing contrast medium and rinsing fluid thus no longer come into direct contact with the examination table, but flow directly onto the sheet and along the length of the sheet into the plastic sack of the collector receptacle.

In an advantageous embodiment of the invention, the uppermost terminal edge of the sheet can also be bonded on itself in a tubular fashion, and, via a drawn-through belt, can be capable of being securely attached to the body of the patient. This embodiment of the sheet of the plastic sack prevents, in a particularly simple fashion, outflowing contrast medium or rinsing fluid from running up, for example, along the back of the patient to be examined, and, from there, reaching the examination table on the other side of the edge of the sheet. A very minimal raising of the patient or a corresponding inclination of the examination table, which need deviate only a few degrees from the horizontal, is already sufficient to be able to avoid with certainty such a smearing of rinsing fluid or contrast medium.

The carrying capacity of the plastic sack can be substantially increased if the sheet, in a particularly expedient further development of the invention, bears an additional tubular bonding forming a sleeve, approximately in the plane of the border of the plastic sack with the sheet, through which sleeve the rod interconnecting both countersupports can be inserted. This has the advantage that the plastic sack is supported virtually on its entire circumference either by the flexible band or by the rod. In addition, the rod thus effectively prevents the weight of the fluid collected in the plastic sack from drawing away the sheet from beneath the patient.

Additional details of the invention shall be explained in greater detail on the basis of a sample embodiment illustrated in the accompanying drawing, and other objects, features and advantages will be apparent from this detailed disclosure and from the appended claims.

BRIEF DESCRIPTION OF THE DRAWINGS

The single FIGURE shows a perspective representation—with parts disengaged and offset for the purpose of a better overview—of the examination table with the inventive collector receptacle.

DETAILED DESCRIPTION

In the FIGURE, it is possible to recognize the end, facing the examining physician, of the patient support platform 1 of a urological examination table 2. The patient support platform 1 is provided, in proximity of its caudal front face 3, with an essentially rectangular depression 4 in which the posterior of the patient to be examined is positioned. The depression 4, at this front side 3 of the patient support platform 1, leads to a type of discharge funnel 5. Beneath the patient support platform, at both sides of its caudal front side 3, one support 6, 7, each, is mounted for a collector receptacle 8. The two supports 6, 7 bear, on their sides facing one another, a horizontal pin 9, 10, each. In addition, the two supports 6, 7, on the same side on which the respective pin is located, are provided with a stopping face 11, 12 aligned perpendicularly to the plane of the patient support platform and parallel to the front side 3 of the patient support platform 1.

The collector receptacle 8 comprises, among other things, a band 15 consisting of spring steel secured at both its ends, on edge, in countersupports 13, 14. The countersupports 13, 14, which are essentially flat bars consisting of plastic, have one central through-extending bore 16, 17, each, which are matched in their diameter to the diameter of the pins 9, 10 on the supports 6, 7. The edge faces 18, 19—not facing the band—of the countersupports 13, 14, are disposed at the same spatial interval from the respective bores 16, 17, as the stopping faces 11, 12, of the supports 6, 7 from the respective pins 9, 10. Moreover, the edge face 18, 19, of each countersupport 13, 14, is strongly beveled at its upper section to provide an additional auxiliary edge face 20, 21, inclined at an angle of 30° relative to the front face. Directly behind the auxiliary edge faces, the two countersupports are slotted, each slot 22, 23 being offset from a respective edge face 18, 19 by an equal distance. Between the bore 16, 17, for the pin 9, 10, and the slot 22, 23, one small blind hole, 24, 25, each, is inserted into the countersupports 13, 14, perpendicular to the direction of the bore 16, 17. The ends of a U-shaped bent rod 26, which have been bent down at an angle of 90°, fit into these blind holes 24, 25. The rod holds the two countersupports 13, 14, in the inserted state, at a mutual spatial interval which prevents disengagement from the pins 9, 10 of the supports 6, 7.

The flexible band 15 is drawn, with its one countersupport, through the semicircularly flanged and bonded edge 27 of a plastic sack 28. The edge 27 of the plastic sack 28 is flanged only at half its circumference for the threading-through of the elastic band 15. The remaining edge of the plastic sack 28 is extended by approximately 70 cm, and, as indicated in the FIGURE, is placed in the form of a sheet 29 on the patient support platform 1. The terminal edge 30 of this sheet 29 is likewise flanged in a tubular fashion. A belt 31 is drawn through this flanged terminal edge. In the plane of the rod 26, sheet 29 bears a tubular bonding 32 forming a sleeve through which the rod can be passed.

In order to prepare for a urological examination, the highly flexible band 15 with the two countersupports 13, 14 fixed to the ends thereof is pushed through the flanged border 27 of the plastic sack 28, so that this flanged border encloses the highly flexible band with the exception of its two countersupports 13, 14. Then the two countersupports 13, 14 are placed over the pins 9, 10 of the support 6, 7 of the patient support platform 1. The countersupports 13, 14 thus rest, with their bores 16, 17 on the pins 9, 10 and are supported with their front face 18, 19 against the stopping face 11, 12 of the respective support. The stopping faces prevent the countersupports with the elastic band 15 from pivoting downwardly about the pins 9, 10, and thus prevent pivoting of the countersupports about their common axis 34 from the horizontal position in a downward direction. The U-shaped rod 26, bent down at an angle at the ends, is now inserted into the two blind holes 24, 25 of the countersupports 13, 14. This rod 26 holds the countersupports 13, 14 at a specified mutual spatial interval and thus prevents them from being able to disengage from the pins 9, 10. At the same time, the torsion resistance of the rod 26 serves to couple the countersupports so that when one of the two countersupports is pivoted simultaneously also the other countersupport is shifted by the same angular amount.

Before rod 26 is inserted into the blind holes 24, 25 of the two countersupports 13, 14, it is inserted through the tubular sleeve 32 in the sheet extension 29 of the plastic sack 28. This section of the plastic sack can thus support itself, via rod 26, on the two countersupports 13, 14. The remaining end of the sheet 29 is placed on the patient support platform 1, and, following positioning of the patient, is secured with the belt 31 extending about the body of the patient. Outflowing rinsing fluid or contrast medium thus no longer directly reaches the patient support platform 1; on the contrary, it flows onto the sheet 29 of the plastic sack 28, and, from there, favored by the funnel-shaped depression 4 of the patient support platform 1, into the plastic sack 28. By virtue of the fact that the sheet is longer than the depression 4 in the patient support platform 1, its termination at the patient-side with belt 31 is disposed higher than the discharge funnel 5 of the depression 4. Outflowing contrast medium and outflowing rinsing fluid accordingly do not run up onto the back of the patient. Through a slight tilting of the examination table or a minimal upright positioning of the patient, this effect can be achieved also without a depression 4 and can be even further intensified.

In order to protect the examining individual from spraying (or splashing) rinsing fluid, the two countersupports 13, 14, can be pivoted upwardly through approximately 30° about pins 9, 10. This is possible owing to the slots 22, 23, in the countersupports 13, 14, which permit a slight resilience of the boundary edge between the each end face 18, 19, and the adjoining auxiliary sloping face 20, 21. Pursuant to swinging-up, the auxiliary edge faces, which are inclined 30° relative to the front faces of the countersupports 13, 14, come into engagement with the stopping faces 11, 12. They arrest the collector receptacle 8 in this upwardly-swung position in which the examining individual is particularly protected. At the same time, the examining individual keeps his hands free for the necessary work to be carried out.

In order to increase the holding capacity of the plastic sack 28, in instances in which a particularly great amount of rinsing fluid is utilized, the plastic sack is provided at its lowest point with a hose fitting 33. This fitting can be coupled to a type of coupling piece similar to those conventional in the case of garden hoses, and the rinsing fluid can be conducted, via a hose (not illustrated) into the drainage system. However, prior to this, the plastic sack must be perforated in the region of the hose fitting 33. However, it is expedient here to employ a strainer over the hose fitting.

During the examination, the plastic sack 28, in spite of its large opening, provides very little interference, because the highly flexible steel band 15 can be pressed back at any time by the examining individual standing in front of it, and it therefore does not obstruct him during examination and during his various undertakings. Also, during tilting of the examination table 2, and in the upright position of the same, there exists no danger that any type of damage will result if the plastic sack rests on the floor of the operating room. In addition, the soft plastic sack 28, in spite of its greater depth, obstructs the knee freedom of the examining individual far less than was the case with the previously employed metallic collector-receptacles.

It will be apparent that many modifications and variations may be effected without departing from the scope of the novel concepts and teachings of the present invention.

I claim as my invention:

1. A urological examination table comprising a patient support platform and comprising a collector-receptacle which can be inserted into two supports at the caudal front side of the patient support platform directly beneath the same, characterized in that the collector receptacle (8) comprises a plastic sack (28) having an elongated upper edge (27) which is flanged in a tubular fashion and which is of a length to extend in a generally semicircular configuration at the region of the plastic sack (28) remote from the patient support platform (1), and a highly flexible band (15) extending on edge, in a substantially horizontal, generally semicircular arch through the flanged upper edge (27) of the plastic sack for supporting the same, said highly flexible band (15) having countersupports (13, 14) secured therewith at opposite lateral sides of the plastic sack (28) for coupling to the supports (6, 7) of the patient support platform (1) such that the elongated upper edge (27) is normally held in said generally semicircular configuration and disposed so as to protrude generally horizontally, said countersupports (13, 14) being disposed when coupled with said supports (6, 7) to accommodate laterally inward deflection of said upper edge (27) in a generally horizontal plane in response to engagement with a physician approaching toward said patient support platform, and said band (15) being of sufficient flexibility to be distortable laterally in a horizontal plane to accommodate such laterally inward deflection of said upper edge (27).

2. A urological examination table according to claim 1, characterized in that the countersupports (13, 14) are pivotally mounted on the supports (6, 7) for movement about a horizontal axis (34), aligned parallel to the caudal front face (3) of the examination table (2).

3. A urological examination table according to claim 1, characterized in that the two supports (6, 7) bear one horizontal pin (9, 10) each, which can be plugged into a corresponding bore (16, 17) of one of the countersupports, and that the countersupports are interconnected via a rod (26) fixing their mutual spatial interval and constraining the countersupports for joint pivotal movement.

4. A urological examination table according to claim 3, characterized in that there is allocated to the two supports (6, 7) one stopping face (11, 12) each, which, for the purpose of arresting the band (15) in the horizontal plane, can be brought into engagement with a corresponding face (18, 19) of the respective countersupport.

5. A urological examination table according to claim 4, characterized in that the stopping faces (11, 12) are aligned parallel to the caudal front side (3) of the examination table (2), and that the countersupports (13, 14), in addition to the front faces (18, 19), allocated to the horizontal position of the band (15), manifest one additional auxiliary face each (20, 21) coming into engagement with the stopping faces pursuant to swinging up the band through about 30°.

6. A urological examination table according to claim 1, characterized in that only a portion of the upper edge (27) of the plastic sack (28) is tubularly flanged, and that another portion of the plastic sack forms an approximately 70-cm-long and approximately 60-cm-wide sheet (29).

7. A urological examination table according to claim 6, characterized in that the uppermost terminal edge (30) of the sheet (29) is formed in a tubular sleeve, and can be fixedly secured to the body of the patient via a belt (31) drawn through said tubular sleeve.

8. A urological examination table according to claim 6, characterized in that the sheet (29), approximately in the plane of the upper edge (27) of the plastic sack (28), bears an additional sleeve (32), and a rod (26) interconnecting both countersupports (13, 14) and extending through said additional sleeve (32).

9. A urological examination table according to claim 1, characterized in that spring steel is utilized as the band material.

10. A urological examination table according to claim 1, characterized in that a flexible synthetic material is utilized as the band material, which, in the region of its upper and lower edge, is reinforced by means of one cast integral wire each.

11. A urological examination table according to claim 1, characterized in that the width of the flanged edge (27) of the plastic sack (28) permits at least one of the countersupports (13, 14) to be threaded therethrough along with said band for engaging the band in supporting relation to said edge.

12. A urological examination table according to claim 1, characterized in that the plastic sack (28), at its deepest location, bears a tubular fitting (33) which can be coupled to a corresponding hose connection piece.

13. A urological examination table comprising a patient support platform and comprising a collector-receptacle which can be secured at the caudal front side of the patient support platform directly beneath the same, characterized in that the collector receptacle (8) comprises a plastic sack (28) having an elongated upper edge (27) which is flanged in a tubular fashion and which is of a length to extend in a generally semicircular configuration at the region of the plastic sack (28) remote from the patient support platform (1), a band (15) having support means (13, 14) for coupling to the patient support platform (1) for supporting said band with said band extending on edge, in a generally horizontal, generally semicircular arch through the flanged upper edge (27) of the plastic sack for supporting the same while accommodating laterally inward deflection of said upper edge (27) in a generally horizontal plane in response to engagement with a physician approaching toward said patient support platform, and said band (15) being of sufficient flexibility to be distortable laterally in a generally horizontal plane to accommodate such laterally inward deflection of said upper edge (27), and further characterized in that said plastic sack (28) has a portion opposite said upper edge (27) for extending in overlying relation to said patient support platform, said portion forming an approximately 70-cm-long and approximately 60-cm-wide sheet (29).

14. A urological examination table according to claim 13, characterized in that the sheet (29), approximately in the plane of the upper edge (27) of the plastic sack (28), bears an additional sleeve (32), and a support rod (26) which is relatively rigid in comparison to said band (15) extending through said additional sleeve (32) and being secured to said support means (13, 14) for said band.

* * * * *